United States Patent [19]
Clayton et al.

[11] Patent Number: 5,582,298
[45] Date of Patent: Dec. 10, 1996

[54] BUSINESS FORM INCLUDING A SAMPLING KIT

[75] Inventors: Melvin T. Clayton, Canyon; Gary Griffith, Amarillo, both of Tex.

[73] Assignee: UARCO Incorporated, Barrington, Ill.

[21] Appl. No.: 442,371

[22] Filed: May 16, 1995

[51] Int. Cl.$^6$ ................................................. B65D 81/00
[52] U.S. Cl. ........................... 206/569; 206/460; 206/778
[58] Field of Search ................................. 206/569, 460, 206/459.5, 775, 776, 777, 778, 782, 813

[56] References Cited

U.S. PATENT DOCUMENTS

| | | | |
|---|---|---|---|
| 3,481,460 | 12/1969 | Watts | 206/460 X |
| 4,317,852 | 3/1982 | Ogden | 206/460 X |
| 4,979,515 | 12/1990 | Briggs et al. | 206/569 X |

Primary Examiner—Jacob K. Ackun
Attorney, Agent, or Firm—Wood, Phillips, VanSanten, Clark & Mortimer

[57] ABSTRACT

An inexpensive, reliable sampling kit made up of a foldable sheet (12) defining a substrate, a die cut opening (30), (32) in the substrate, a transparent cover (34), (36) for the opening (30), (32) and adhered to the sheet on one side thereof, and an adhesive area (40) on the sheet (12) adjacent the opening (30), (32) and containing a layer of pressure sensitive adhesive (52). A removable release liner (60) covers the layer of adhesive (52) and a line of weakening (20), (22) is located in the sheet (12) and extends through the adhesive area (40) in the general direction of the opening (30), (32). The material to be sampled may be adhered to the adhesive area (40) after removal of the release liner (60) so as to extend over the opening (30), (32) and the sheet (12) folded upon itself on the line of weakening (20), (22) and held folded upon itself by the adhesive (52).

16 Claims, 1 Drawing Sheet

BUSINESS FORM INCLUDING A SAMPLING KIT

FIELD OF THE INVENTION

This invention relates to a combined business form and sampling kit. More specifically, it relates to a sampling kit that may be used in collecting samples for subsequent analysis and for transporting such samples to the place of analysis.

BACKGROUND OF THE INVENTION

Samples of organic matter taken from animals are frequently taken for analysis for a large variety of purposes. For example, in the case of tracking parentage of purebred animals, it has been customary to draw blood samples from the animal. The sampled blood is stored in vials which are then transmitted to a laboratory for analysis, typically a DNA analysis.

While the procedure works well for its intended purposes, vials are fragile and therefore, care must be taken in transporting them from the site of sampling to the site of analysis. Furthermore, animal fluids such as blood may degrade if not kept under the proper conditions with the consequence that there is a possibility that any subsequent analysis performed on a degraded sample may not be entirely accurate.

It is also desirable to "archive" samples. That is to say duplicate samples are taken with one being analyzed and the other one stored in the archives of the examining organization for subsequent analysis, if it becomes necessary for any reason. Again, providing archives to hold vials of animal fluids and preserve them in sufficiently good condition that they can be reliably analyzed at some undetermined point in the future is a difficult thing to do.

One organic substance, virtually universally found on all mammals, is hair; and DNA sampling of hair can reliably identify a given animal and provide considerable additional information that may be of relevance to animal breeders or the like. However, using hair as the sample to be analyzed requires an entirely different means of sampling; and the present invention is directed to providing such a means in the form of a sampling kit that is inexpensive, of minimal bulk, that is not fragile, and which may be easily and reliably used.

SUMMARY OF THE INVENTION

It is the principal object of the invention to provide a new and improved sampling kit. More specifically, it is an object of the invention to provide a sampling kit for hair or the like whereby a sample may be obtained, contained and transported for analysis in a simple and inexpensive manner.

An exemplary embodiment of the invention achieves the foregoing object in a sampling kit that includes a sheet of foldable material. Means are provided to define a transparent window in the sheet and an adhesive area is located adjacent the window defining means and includes a layer of pressure sensitive adhesive. A removable release liner means covers the pressure sensitive adhesive and a line of weakening is disposed in the sheet and extends through the adhesive area in the general direction of the opening.

As a consequence, the material to be sampled may be adhered to the adhesive area after removal of the release liner so as to extend over the window and the sheet then folded upon itself on the line of weakening and held together by the adhesive in condition for transportation to a point of analysis.

In a preferred embodiment, the window defining means is provided by a die cut opening in the sheet and a transparent cover for the opening and secured to the sheet on one side thereof.

In one embodiment of the invention, the line of weakening is positioned to intersect the opening in the sheet.

In a highly preferred embodiment, the line of weakening generally bisects both the adhesive area and the opening.

In one embodiment of the invention, the adhesive area and the release liner are defined by a pressure sensitive adhesive label having a release liner and tipped onto the sheet adjacent the opening with the label abutting the substrate to be sandwiched between the substrate and the release liner.

In one embodiment of the invention, there is included an additional line of weakening in the sheet which defines a certificate section and indicia is placed on the certificate section providing for the addition of information relative to the sample.

A highly preferred embodiment of the invention includes two openings that are formed by die cuts and two of the covers, one for each of the openings. The adhesive area is adjacent to each of the openings and there are two of the lines of weakening, one for each of the openings. The lines of weakening are spaced from one another.

Other objects and advantages will become apparent from the following specification taken with the accompanying drawings.

DESCRIPTION OF THE PREFERRED EMBODIMENT

Figure 1:
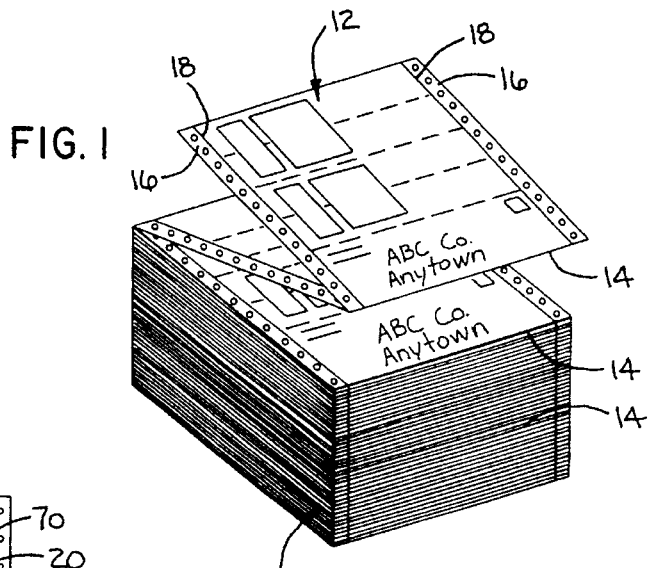
FIG. 1 is a perspective view of a sampling kit in business form style made according to the invention.

An exemplary embodiment of a sampling kit made according to the invention is illustrated in the drawings and as will be apparent from the following description, is basically a business form modified to be usable as a sampling kit. A zig-zag folded stack, generally designated 10, of the sampling kits is illustrated. The stack is formed of an elongated web, typically but not necessarily opaque of paper, card stock, or the like and generally designated 12, folded on transverse lines of weakening 14 into the zig zag stack. Longitudinal edges of the ply 12 are provided with conventional control punch margins 16 that are used in the manufacture of the sampling kit. Longitudinal lines of weakening 18, typically perforations, allow separation of the control punch margins 16 from the remainder of the form.

Figure 2:
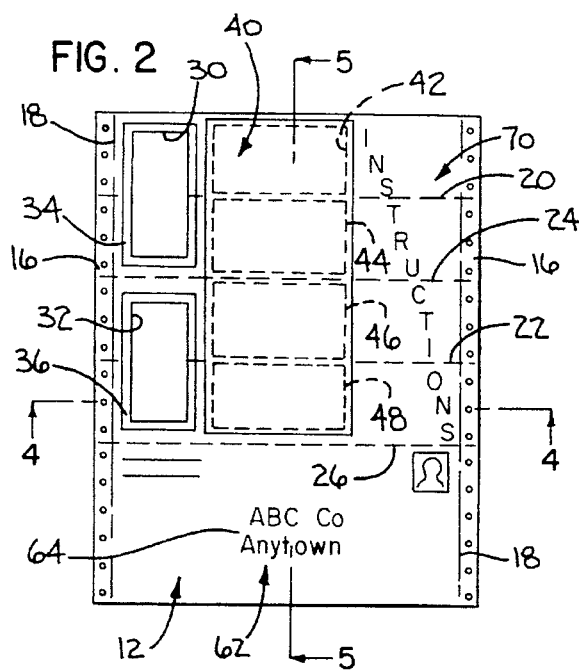
FIG. 2 is a plan view of one form length of the business form-sampling kit.
Figure 3:
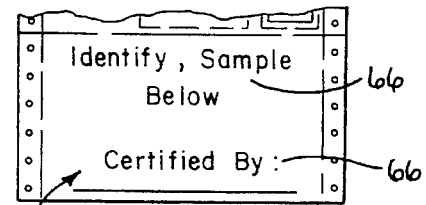
FIG. 3 is a fragmentary view of the backside of part of the business form-sampling kit.

FIG. 2 is a plan view of one form length of the business form. As can be seen, the same includes a first transverse line of weakening 20, a second transverse line of weakening 22, a third transverse line of weakening 24 and a fourth transverse line of weakening 26. As is typical, these transverse lines of weakening 20, 22, 24, 26 are made up of perforations in the web 12.

The components of the sampling kit are intended to be separated from one another along the transverse lines of weakening 24 and 26 whereas the transverse lines of weakening 20 and 22 simply serve as folding points.

The transverse lines of weakening 24 and 26 are located so as to divide an individual form length of the ply 12 into three approximately equal parts while the transverse lines of weakening 20 and 22 divide each such part in half, that is, they bisect their associated part.

Figure 4:
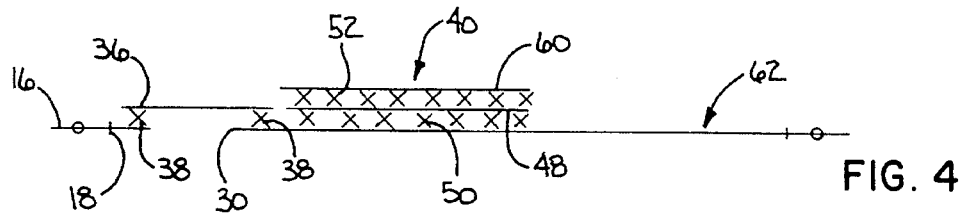
FIG. 4 is a schematic sectional view taken along the line 4—4 in FIG. 2.

Adjacent the left hand control punch margin 16, the ply 12 includes a first, elongated, rectangular die cut 30 and a second, identical die cut 32. The die cuts 30 and 32 are located to the same side of the transverse line of weakening 26. Both are covered by respective transparent covers 34 and 36 which are secured to one side of the ply 12 by a suitable adhesive 38 (see FIG. 4). The structure is much like that of a covered window in a so-called "window" envelope although it is preferred that a perfectly clear cover 34, 36 be utilized rather than using some of the more cloudy glassine type covers found on some window envelopes.

Adjacent to the die cut openings 30 and 32 is an adhesive area, generally designated 40. In the adhesive area 40 a plurality of four pressure sensitive adhesive labels 42, 44, 46, 48 are tipped on to the web 12 and secured in place by adhesive 50. The labels are tipped on via any conventional means and are provided with pressure sensitive adhesive 52 on their sides opposite the web 12.

A preferred pressure sensitive adhesive for the adhesive 52 will not interfere with any contemplated analysis of the sample. When hair is to be subjected to DNA analysis, adhesive R555 available from S. D. Warren Company of Westbrook, Me. may be used.

Figure 5:
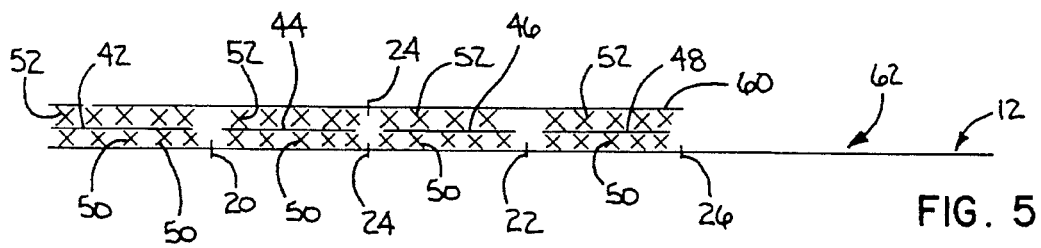
FIG. 5 is a schematic sectional view taken approximately along the line 5—5 in FIG. 2.

Furthermore, the individual labels 42, 44, 46, 48 are located so as to be separated by the transverse lines of weakening 20, 24, 22 and to one side of the transverse line of weakening 26 as seen in FIG. 5.

A common release liner 60 is removably adhered to the pressure sensitive adhesive 52 so as to sandwich the labels 42, 44, 46, 48 against the web 12. If desired, as illustrated in FIG. 5, the release liner 60 may have the line of perforation 24 extending through the same.

That part of the form below the transverse line of weakening 26 as shown in FIG. 2 is designated as a certificate section, generally designated 62. As seen in FIG. 2, a mailing address or other suitable indicia 64 may be placed thereon indicating an address to which the certificate section 62 may be sent after being detached from the remainder of the form on the transverse line of weakening 26. The opposite side of the certificate section 62 may be provided with indicia 66 that directs the user to provide additional information that is relative to the sample to be taken when the device is being used.

The form is completed by an instruction section, generally designated 70 to one side of the adhesive area 40, and specifically, the side of the adhesive area 40 remote from the openings 30, 32. In the area 70, suitable instructions on the use of the form may be provided.

In the usual case, a hair sample will be taken from an animal and will be such that the roots remain on the shafts of the hair. The release liner 60 will be removed and the hair sample divided in two to provide two half samples.

The shafts of one half sample may be adhered to the pressure sensitive adhesive 52 on the label section 42 in such a way that the hair roots overlie the window or opening 30. The other half sample may similarly be applied to the form by adhering the shafts to the label section 46, again so that the roots overlie the adjacent window or opening 32.

Assuming that the certificate section 62 has been removed, the form may then be folded upon the line of weakening 20 so as to bring the label 42 and its adhesive 52 into contact with the label and its adhesive 52. This will hold the form in the folded relation while enclosing one half sample such that the roots are visible from either side through the opening 30 but not exposed therethrough by reason of the presence of the transparent layer 34. Similarly, the bottom part of the form may be folded on the fold line 22 to bring the adhesive 52 on the label 48 into contact with the adhesive 52 on the label 46 so that the half sample contained thereon will similarly be enclosed, with the roots visible through the opening 32 but protected by the transparent layer 36.

With the control punch margins 18 removed, the same may be placed in any suitable business envelope, such as a preaddressed envelope and sent to a laboratory that will then analyze the sample as desired.

In this regard, the use of the windows defined by the openings 30, 32 with the protective transparent layers 34, 36 allows the laboratory to either manually, or automatically with the use of appropriate automated equipment, observe the sample, specifically the roots of the hair shafts, and, to the extent necessary, remove the same from the sampling device through partial or entire removal of the transparent labels 34 or 36 so that the analysis on the sample may then be performed.

Though not necessary to the invention, it is preferred that the form have means for providing what amounts to two distinct samples (each referred to earlier as a "half sample") to the analysis laboratory. As a consequence, upon its arrival, the two samples may be separated along the transverse line of weakening 24 with one of the samples being provided to the laboratory for immediate analysis and the other sample being submitted to the laboratory archives to be saved for possible future use.

From the foregoing, it will be readily appreciated that a sampling kit made according to the invention is quite inexpensive to fabricate and easy to use. And while the same has been disclosed in connection with the obtaining and analysis of hair samples, it should be appreciated that the invention is not so limited. For example, the adhesive 50 could be utilized to capture test strips utilized for sampling any of a variety of liquids or fluids including those that don't even originate with animals.

We claim:

1. A sampling kit comprising:

a foldable sheet defining a substrate;

a die cut opening in said substrate;

a transparent cover for said opening and adhered to said sheet on one side thereof;

an adhesive area on said sheet adjacent said opening and containing a layer of pressure sensitive adhesive;

a removable release liner covering said layer; and a line of weakening in said sheet extending through said area in the general direction of said opening;

whereby material to be sampled may be adhered to said area after removal of said release liner so as to extend over said opening and the sheet folded upon itself on said line of weakening and held folded upon itself by said adhesive.

2. The sampling kit of claim 1 wherein said line of weakening is positioned to intersect said opening.

3. The sampling kit of claim 2 wherein said line of weakening generally bisects said area and opening.

4. The sampling kit of claim 1 wherein said adhesive area and said release liner are defined by a pressure sensitive adhesive label having a release liner and tipped onto said sheet adjacent said opening with the label abutting said substrate to be sandwiched between said substrate to said release liner.

5. The sampling kit of claim 1 further including an additional line of weakening in said sheet to define a certificate section; and indicia on said certificate section providing for the addition of information relative to the sample.

6. The sampling kit of claim 1 further including two of said die cut openings and two of said covers, one for each opening, said adhesive area being adjacent each of said openings, there further being two of said lines of weakening, one for each of said openings, said lines of weakening being spaced from one another.

7. A sampling kit comprising:

a foldable sheet made of paper, card stock or the like;

a pair of window means in said sheet at spaced locations;

transparent covers for said window means and secured to said sheet;

an adhesive area adjacent each of said window means, each including a layer of pressure sensitive adhesive;

removable release liner means covering said pressure sensitive adhesive; and first and second spaced lines of weakening in said sheet, each extending generally in the direction of an associated one of said pair of window means.

8. The sampling kit of claim 7 wherein each of said window means is defined by a single opening in said sheet.

9. The sampling kit of claim 7 further including a third line of weakening located between said first and second lines of weakening and extending between the window means of said pair.

10. The sampling kit of claim 9 further including an additional line of weakening in said sheet to define a certificate section; and indicia on said certificate section providing for the addition of information relative to the sample.

11. The sampling kit of claim 7 wherein said pair of window means is defined by only two separate openings in said sheet.

12. A sampling kit comprising:

a sheet of foldable material;

means defining a transparent window in said sheet;

an adhesive area adjacent said window defining means and including a layer of pressure sensitive adhesive;

removable release liner means covering said pressure sensitive adhesive; and first and second spaced lines of weakening in said sheet, said lines being generally parallel and extending across said sheet generally in the direction of said window defining means.

13. The sampling kit of claim 12 further including a third line of weakening between and generally parallel to said first and second lines of weakening.

14. The sampling kit of claim 12 wherein said material also is opaque.

15. The sampling kit of claim 12 wherein said window defining means includes at least one opening in said sheet and a transparent cover over said opening and secured to said sheet.

16. A continuous business form construction made of an interconnected plurality of said sampling kits of claim 12 in a zig zag folded stack.

* * * * *